(12) United States Patent
Clemow et al.

(10) Patent No.: US 7,799,084 B2
(45) Date of Patent: Sep. 21, 2010

(54) MODULAR FEMORAL COMPONENT FOR A TOTAL KNEE JOINT REPLACEMENT FOR MINIMALLY INVASIVE IMPLANTATION

(75) Inventors: Alastair J. T. Clemow, Princeton, NJ (US); Dana C. Mears, Pittsburgh, PA (US)

(73) Assignee: Mako Surgical Corp., Ft. Lauderdale, FL (US)

( * ) Notice: Subject to any disclaimer, the term of this patent is extended or adjusted under 35 U.S.C. 154(b) by 1028 days.

(21) Appl. No.: 10/532,409

(22) PCT Filed: Oct. 23, 2003

(86) PCT No.: PCT/US03/33641

§ 371 (c)(1),
(2), (4) Date: Sep. 26, 2005

(87) PCT Pub. No.: WO2004/037119

PCT Pub. Date: May 6, 2004

(65) Prior Publication Data

US 2006/0155380 A1    Jul. 13, 2006

Related U.S. Application Data

(60) Provisional application No. 60/420,299, filed on Oct. 23, 2002.

(51) Int. Cl.
*A61F 2/38* (2006.01)
(52) U.S. Cl. .................................................. 623/20.15
(58) Field of Classification Search ............. 623/20.35, 623/20.36, 20.14, 20.15, 20.19, 20.2, 22.42, 623/20.11, 18.11
See application file for complete search history.

(56) References Cited

U.S. PATENT DOCUMENTS

| 3,953,899 A | 5/1976 | Charnley |
| 4,081,866 A | 4/1978 | Upshaw et al. |

(Continued)

FOREIGN PATENT DOCUMENTS

EP    0 378 928 A    7/1990

(Continued)

OTHER PUBLICATIONS

Supplementary European Search Report mailed Dec. 1, 2008 in European Application No. 03 78 1370.

*Primary Examiner*—Eduardo C Robert
*Assistant Examiner*—David Comstock
(74) *Attorney, Agent, or Firm*—Foley & Lardner LLP

(57) ABSTRACT

A femoral component (100) for a total knee joint replacement has a modular structure including a number of segments (102, 112), each of the segments (102, 112) having a femoral fixation surface (104, 114) for attachment to the distal end of a femur and at least one assembly surface (108) for joining with an adjacent segment (102, 112) of the modular femoral component (100). The assembly surfaces (108) are generally planar and arranged to be oriented generally in a plane extending in a proximal-distal direction and in an anterior-posterior direction when the femoral fixation surface (104, 114) is positioned on the distal end of the femur. Although the assembly surfaces (108) are generally planar, they may be shaped or provided with complementary structures (120) to assure self-alignment when the segments (102, 112) are assembled.

16 Claims, 4 Drawing Sheets

U.S. PATENT DOCUMENTS

| | | |
|---|---|---|
| 4,166,292 A | 9/1979 | Bokros |
| 4,207,627 A | 6/1980 | Cloutier |
| 4,211,228 A | 7/1980 | Cloutier |
| 4,220,146 A | 9/1980 | Cloutier |
| 4,309,778 A | 1/1982 | Buechel et al. |
| 4,338,925 A | 7/1982 | Miller |
| 4,340,978 A | 7/1982 | Buechel et al. |
| 4,404,691 A | 9/1983 | Buning et al. |
| 4,467,801 A | 8/1984 | Whiteside |
| 4,474,177 A | 10/1984 | Whiteside |
| 4,501,266 A | 2/1985 | McDaniel |
| 4,506,673 A | 3/1985 | Bonnell |
| 4,574,794 A | 3/1986 | Cooke et al. |
| 4,578,081 A | 3/1986 | Harder et al. |
| 4,646,729 A | 3/1987 | Kenna et al. |
| 4,650,490 A | 3/1987 | Figgie, III |
| 4,653,488 A | 3/1987 | Kenna |
| 4,673,408 A | 6/1987 | Grobbelaar |
| 4,714,474 A | 12/1987 | Brooks, Jr. et al. |
| 4,718,413 A | 1/1988 | Johnson |
| 4,719,908 A | 1/1988 | Averill et al. |
| 4,731,086 A | 3/1988 | Whiteside et al. |
| 4,743,261 A | 5/1988 | Epinette |
| 4,759,350 A | 7/1988 | Dunn et al. |
| 4,764,171 A | 8/1988 | Harder et al. |
| 4,769,040 A | 9/1988 | Wevers |
| 4,787,383 A | 11/1988 | Kenna |
| 4,790,854 A | 12/1988 | Harder et al. |
| 4,791,919 A | 12/1988 | Elloy et al. |
| 4,822,366 A | 4/1989 | Bolesky |
| 4,825,857 A | 5/1989 | Kenna |
| 4,834,081 A | 5/1989 | Van Zile |
| 4,850,354 A | 7/1989 | McGurk-Burleson et al. |
| 4,867,155 A | 9/1989 | Isaacson |
| 4,923,472 A | 5/1990 | Ugolini |
| 4,936,847 A | 6/1990 | Manginelli |
| 4,936,853 A | 6/1990 | Fabian et al. |
| 4,938,762 A | 7/1990 | Wehrli |
| 4,938,769 A | 7/1990 | Shaw |
| 4,944,756 A | 7/1990 | Kenna |
| 4,944,757 A | 7/1990 | Martinez et al. |
| 4,944,760 A | 7/1990 | Kenna |
| 4,950,298 A | 8/1990 | Gustilo et al. |
| 4,963,152 A | 10/1990 | Hofmann et al. |
| 4,979,949 A | 12/1990 | Matsen, III et al. |
| 4,985,037 A | 1/1991 | Petersen |
| 5,002,547 A | 3/1991 | Poggie et al. |
| 5,007,933 A | 4/1991 | Sidebotham et al. |
| 5,019,103 A | 5/1991 | Van Zile et al. |
| 5,021,061 A | 6/1991 | Wevers et al. |
| 5,035,700 A | 7/1991 | Kenna |
| 5,037,423 A | 8/1991 | Kenna |
| 5,037,439 A | 8/1991 | Albrektsson et al. |
| 5,047,032 A | 9/1991 | Jellicoe |
| 5,061,271 A | 10/1991 | Van Zile |
| 5,074,880 A | 12/1991 | Mansat |
| 5,086,401 A | 2/1992 | Glassman et al. |
| 5,098,436 A | 3/1992 | Ferrante et al. |
| 5,100,409 A | 3/1992 | Coates et al. |
| 5,108,398 A | 4/1992 | McQueen et al. |
| 5,116,338 A | 5/1992 | Poggie et al. |
| 5,122,144 A | 6/1992 | Bert et al. |
| 5,129,907 A | 7/1992 | Heldreth et al. |
| 5,129,909 A | 7/1992 | Sutherland |
| 5,133,759 A | 7/1992 | Turner |
| 5,133,760 A | 7/1992 | Petersen et al. |
| 5,147,403 A | 9/1992 | Gitelis |
| 5,147,406 A | 9/1992 | Houston et al. |
| 5,152,795 A | 10/1992 | Sioshansi et al. |
| 5,152,796 A | 10/1992 | Slamin |
| 5,152,797 A | 10/1992 | Luckman et al. |
| 5,154,717 A | 10/1992 | Matsen, III et al. |
| 5,171,244 A | 12/1992 | Caspari et al. |
| 5,171,276 A | 12/1992 | Caspari et al. |
| 5,176,683 A | 1/1993 | Kimsey et al. |
| 5,176,684 A | 1/1993 | Ferrante et al. |
| 5,176,710 A | 1/1993 | Hahn et al. |
| 5,180,384 A | 1/1993 | Mikhail |
| 5,181,925 A | 1/1993 | Houston et al. |
| 5,194,066 A | 3/1993 | Van Zile |
| 5,197,986 A | 3/1993 | Mikhail |
| 5,201,768 A | 4/1993 | Caspari et al. |
| 5,203,807 A | 4/1993 | Evans et al. |
| 5,207,711 A | 5/1993 | Caspari et al. |
| 5,217,463 A | 6/1993 | Mikhail |
| 5,219,362 A | 6/1993 | Tuke et al. |
| 5,222,955 A | 6/1993 | Mikhail |
| 5,226,915 A | 7/1993 | Bertin |
| 5,226,916 A | 7/1993 | Goodfellow et al. |
| 5,228,459 A | 7/1993 | Caspari et al. |
| 5,234,433 A | 8/1993 | Bert et al. |
| 5,236,432 A | 8/1993 | Matsen, III et al. |
| 5,236,462 A | 8/1993 | Mikhail |
| 5,246,459 A | 9/1993 | Elias |
| 5,250,050 A | 10/1993 | Poggie et al. |
| 5,251,127 A | 10/1993 | Raab |
| 5,258,032 A | 11/1993 | Bertin |
| 5,263,498 A | 11/1993 | Caspari et al. |
| 5,271,737 A | 12/1993 | Baldwin et al. |
| 5,284,482 A | 2/1994 | Mikhail |
| 5,290,290 A | 3/1994 | Mikhail |
| 5,299,288 A | 3/1994 | Glassman et al. |
| 5,300,120 A | 4/1994 | Knapp et al. |
| 5,304,181 A | 4/1994 | Caspari et al. |
| 5,305,203 A | 4/1994 | Raab |
| 5,308,349 A | 5/1994 | Mikhail |
| 5,308,350 A | 5/1994 | Mikhail |
| 5,312,411 A | 5/1994 | Steele et al. |
| 5,314,482 A | 5/1994 | Goodfellow et al. |
| 5,322,506 A | 6/1994 | Kullas |
| 5,326,363 A | 7/1994 | Aikins |
| 5,330,534 A | 7/1994 | Herrington et al. |
| 5,334,194 A | 8/1994 | Mikhail |
| 5,336,266 A | 8/1994 | Caspari et al. |
| 5,344,458 A | 9/1994 | Bonutti |
| 5,344,461 A | 9/1994 | Phlipot |
| 5,358,525 A | 10/1994 | Fox et al. |
| 5,358,527 A | 10/1994 | Forte |
| 5,358,529 A | 10/1994 | Davidson |
| 5,358,531 A | 10/1994 | Goodfellow et al. |
| 5,364,401 A | 11/1994 | Ferrante et al. |
| 5,370,693 A | 12/1994 | Kelman et al. |
| 5,370,694 A | 12/1994 | Davidson |
| 5,370,699 A | 12/1994 | Hood et al. |
| 5,380,331 A | 1/1995 | Mikhail |
| 5,380,332 A | 1/1995 | Ferrante |
| 5,383,937 A | 1/1995 | Mikhail |
| 5,387,241 A | 2/1995 | Hayes |
| 5,395,376 A | 3/1995 | Caspari et al. |
| 5,395,401 A | 3/1995 | Bahler |
| 5,397,330 A | 3/1995 | Mikhail |
| 5,397,360 A | 3/1995 | Cohen et al. |
| 5,405,395 A | 4/1995 | Coates |
| 5,405,396 A | 4/1995 | Heldreth et al. |
| 5,408,409 A | 4/1995 | Glassman et al. |
| 5,413,605 A | 5/1995 | Ashby et al. |
| 5,413,606 A | 5/1995 | Fisk et al. |
| 5,415,662 A | 5/1995 | Ferrante et al. |
| 5,415,704 A | 5/1995 | Davidson |
| 5,423,822 A | 6/1995 | Hershberger et al. |
| 5,423,828 A | 6/1995 | Benson |
| 5,425,775 A | 6/1995 | Kovacevic et al. |
| 5,431,653 A | 7/1995 | Callaway |
| 5,437,630 A | 8/1995 | Daniel et al. |

| Patent No. | Date | Inventor |
|---|---|---|
| 5,443,512 A | 8/1995 | Parr et al. |
| 5,445,642 A | 8/1995 | McNulty et al. |
| 5,457,891 A | 10/1995 | Taylor |
| 5,458,644 A | 10/1995 | Grundei |
| 5,458,645 A | 10/1995 | Bertin |
| 5,470,354 A | 11/1995 | Hershberger et al. |
| 5,474,559 A | 12/1995 | Bertin et al. |
| 5,480,443 A | 1/1996 | Elias |
| 5,480,444 A | 1/1996 | Incavo et al. |
| 5,480,446 A | 1/1996 | Goodfellow et al. |
| 5,486,177 A | 1/1996 | Mumme et al. |
| 5,486,178 A | 1/1996 | Hodge |
| 5,509,934 A | 4/1996 | Cohen |
| 5,514,139 A | 5/1996 | Goldstein et al. |
| 5,514,143 A | 5/1996 | Bonutti et al. |
| 5,520,693 A | 5/1996 | McGuire et al. |
| 5,520,694 A | 5/1996 | Dance et al. |
| 5,540,695 A | 7/1996 | Levy |
| 5,542,947 A | 8/1996 | Treacy |
| 5,549,683 A | 8/1996 | Bonutti |
| 5,549,686 A | 8/1996 | Johnson et al. |
| 5,549,687 A | 8/1996 | Coates et al. |
| 5,549,688 A | 8/1996 | Ries et al. |
| 5,556,429 A | 9/1996 | Felt |
| 5,556,433 A | 9/1996 | Gabriel et al. |
| 5,569,259 A | 10/1996 | Ferrante et al. |
| 5,570,706 A | 11/1996 | Howell |
| 5,571,110 A | 11/1996 | Matsen, III et al. |
| 5,571,194 A | 11/1996 | Gabriel |
| 5,575,793 A | 11/1996 | Carls et al. |
| 5,578,039 A | 11/1996 | Vendrely et al. |
| 5,593,450 A | 1/1997 | Scott et al. |
| 5,593,719 A | 1/1997 | Dearnaley et al. |
| 5,597,379 A | 1/1997 | Haines et al. |
| 5,601,566 A | 2/1997 | Dance et al. |
| 5,606,590 A | 2/1997 | Petersen et al. |
| 5,609,640 A | 3/1997 | Johnson |
| 5,609,641 A | 3/1997 | Johnson et al. |
| 5,609,642 A | 3/1997 | Johnson et al. |
| 5,609,643 A | 3/1997 | Colleran et al. |
| 5,609,645 A | 3/1997 | Vinciguerra |
| 5,611,353 A | 3/1997 | Dance et al. |
| 5,613,970 A | 3/1997 | Houston et al. |
| 5,616,146 A | 4/1997 | Murray |
| 5,628,749 A | 5/1997 | Vendrely et al. |
| 5,630,820 A | 5/1997 | Todd |
| 5,649,929 A | 7/1997 | Callaway |
| 5,658,344 A | 8/1997 | Hurlburt |
| 5,667,511 A | 9/1997 | Vendrely et al. |
| 5,667,512 A | 9/1997 | Johnson |
| 5,681,289 A | 10/1997 | Wilcox et al. |
| 5,681,316 A | 10/1997 | DeOrio et al. |
| 5,681,354 A | 10/1997 | Eckhoff |
| 5,682,886 A | 11/1997 | Delp et al. |
| 5,683,469 A | 11/1997 | Johnson et al. |
| 5,683,470 A | 11/1997 | Johnson et al. |
| 5,683,471 A | 11/1997 | Incavo et al. |
| 5,683,472 A | 11/1997 | O'Neil et al. |
| 5,688,279 A | 11/1997 | McNulty et al. |
| 5,688,280 A | 11/1997 | Booth, Jr. et al. |
| 5,688,281 A | 11/1997 | Cripe et al. |
| 5,688,282 A | 11/1997 | Baron et al. |
| 5,690,635 A | 11/1997 | Matsen, III et al. |
| 5,690,636 A | 11/1997 | Wildgoose et al. |
| 5,702,460 A | 12/1997 | Carls et al. |
| 5,702,463 A | 12/1997 | Pothier et al. |
| 5,702,464 A | 12/1997 | Lackey et al. |
| 5,702,467 A | 12/1997 | Gabriel et al. |
| 5,716,360 A | 2/1998 | Baldwin et al. |
| 5,716,361 A | 2/1998 | Masini et al. |
| 5,728,162 A | 3/1998 | Eckhoff |
| 5,733,292 A | 3/1998 | Gustilo et al. |
| 5,741,264 A | 4/1998 | Cipolletti |
| 5,743,915 A | 4/1998 | Bertin et al. |
| 5,748,767 A | 5/1998 | Raab |
| 5,749,876 A | 5/1998 | Duvillier et al. |
| 5,755,800 A | 5/1998 | O'Neil et al. |
| 5,755,803 A | 5/1998 | Haines et al. |
| 5,766,255 A | 6/1998 | Slamin et al. |
| 5,769,855 A | 6/1998 | Bertin et al. |
| 5,776,137 A | 7/1998 | Katz |
| 5,776,200 A | 7/1998 | Johnson et al. |
| 5,776,201 A | 7/1998 | Colleran et al. |
| 5,782,920 A | 7/1998 | Colleran |
| 5,782,921 A | 7/1998 | Colleran et al. |
| 5,782,925 A | 7/1998 | Collazo et al. |
| 5,788,700 A | 8/1998 | Morawa et al. |
| 5,795,353 A | 8/1998 | Felt |
| 5,800,438 A | 9/1998 | Tuke et al. |
| 5,800,552 A | 9/1998 | Forte |
| 5,806,518 A | 9/1998 | Mittelstadt |
| 5,810,827 A | 9/1998 | Haines et al. |
| 5,824,096 A | 10/1998 | Pappas et al. |
| 5,824,097 A | 10/1998 | Gabriel et al. |
| 5,824,103 A | 10/1998 | Williams |
| 5,824,104 A | 10/1998 | Tuke |
| 5,824,105 A | 10/1998 | Ries et al. |
| 5,830,216 A | 11/1998 | Insall et al. |
| 5,853,415 A | 12/1998 | Bertin et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,871,541 A | 2/1999 | Gerber |
| 5,871,542 A | 2/1999 | Goodfellow et al. |
| 5,871,545 A | 2/1999 | Goodfellow et al. |
| 5,871,546 A | 2/1999 | Colleran et al. |
| 5,876,460 A | 3/1999 | Bloebaum |
| 5,879,354 A | 3/1999 | Haines et al. |
| 5,879,389 A | 3/1999 | Koshino |
| 5,879,391 A | 3/1999 | Slamin |
| 5,879,392 A | 3/1999 | McMinn |
| 5,879,394 A | 3/1999 | Ashby et al. |
| 5,880,976 A | 3/1999 | DiGioia, III et al. |
| 5,885,296 A | 3/1999 | Masini |
| 5,891,101 A | 4/1999 | Wilcox et al. |
| 5,895,375 A | 4/1999 | Wilcox et al. |
| 5,897,559 A | 4/1999 | Masini |
| 5,908,424 A | 6/1999 | Bertin et al. |
| 5,911,723 A | 6/1999 | Ashby et al. |
| 5,916,219 A | 6/1999 | Matsuno et al. |
| 5,916,220 A | 6/1999 | Masini |
| 5,925,049 A | 7/1999 | Gustilo et al. |
| 5,928,286 A | 7/1999 | Ashby et al. |
| 5,935,132 A | 8/1999 | Bettuchi et al. |
| 5,937,530 A | 8/1999 | Masson |
| 5,944,722 A | 8/1999 | Masini |
| 5,944,723 A | 8/1999 | Colleran et al. |
| 5,944,756 A | 8/1999 | Fischetti et al. |
| 5,947,973 A | 9/1999 | Masini |
| 5,954,724 A | 9/1999 | Davidson |
| 5,968,051 A | 10/1999 | Luckman et al. |
| 5,971,989 A | 10/1999 | Masini |
| 5,976,147 A | 11/1999 | LaSalle et al. |
| 5,984,969 A | 11/1999 | Matthews et al. |
| 5,997,543 A | 12/1999 | Truscott |
| 5,997,545 A | 12/1999 | Doherty et al. |
| 5,997,577 A | 12/1999 | Herrington et al. |
| 6,002,859 A | 12/1999 | DiGioia, III et al. |
| 6,004,351 A | 12/1999 | Tomita et al. |
| 6,004,352 A | 12/1999 | Buni |
| 6,010,509 A | 1/2000 | Delgado et al. |
| 6,013,081 A | 1/2000 | Burkinshaw et al. |
| 6,019,767 A | 2/2000 | Howell |
| 6,019,794 A | 2/2000 | Walker |
| 6,024,746 A | 2/2000 | Katz |
| 6,033,415 A | 3/2000 | Mittelstadt et al. |

| | | | | | | | |
|---|---|---|---|---|---|---|---|
| 6,042,262 | A | 3/2000 | Hajianpour | 6,355,705 | B1 | 3/2002 | Bond et al. |
| 6,042,584 | A | 3/2000 | Pierson, III | 6,361,731 | B1 | 3/2002 | Smith et al. |
| 6,045,581 | A | 4/2000 | Burkinshaw | 6,371,934 | B1 | 4/2002 | Jackson et al. |
| 6,051,751 | A | 4/2000 | Sioshansi et al. | 6,379,367 | B1 | 4/2002 | Vibe-Hansen et al. |
| 6,056,754 | A | 5/2000 | Haines et al. | 6,379,388 | B1 | 4/2002 | Ensign et al. |
| 6,059,788 | A | 5/2000 | Katz | 6,379,741 | B1 | 4/2002 | Komvopoulos et al. |
| 6,068,633 | A | 5/2000 | Masini | 6,402,786 | B1 | 6/2002 | Insall et al. |
| 6,071,311 | A | 6/2000 | O'Neil et al. | 6,409,852 | B1 | 6/2002 | Lin et al. |
| 6,074,424 | A | 6/2000 | Perrone, Jr. et al. | 6,413,215 | B1 | 7/2002 | Wu et al. |
| 6,077,269 | A | 6/2000 | Masini | 6,413,279 | B1 | 7/2002 | Metzger et al. |
| 6,077,270 | A | 6/2000 | Katz | 6,424,333 | B1 | 7/2002 | Tremblay et al. |
| 6,090,114 | A | 7/2000 | Matsuno et al. | 6,428,577 | B1 | 8/2002 | Evans et al. |
| 6,090,144 | A | 7/2000 | Letot et al. | 6,428,579 | B1 | 8/2002 | Valentini |
| 6,096,043 | A | 8/2000 | Techiera et al. | 6,430,434 | B1 | 8/2002 | Mittelstadt |
| 6,096,082 | A | 8/2000 | Stegmüller et al. | 6,436,145 | B1 | 8/2002 | Miller |
| 6,099,570 | A | 8/2000 | Livet et al. | 6,447,448 | B1 | 9/2002 | Ishikawa et al. |
| 6,102,916 | A | 8/2000 | Masini | 6,447,549 | B1 | 9/2002 | Taft |
| 6,102,952 | A | 8/2000 | Koshino | 6,450,978 | B1 | 9/2002 | Brosseau et al. |
| 6,106,529 | A | 8/2000 | Techiera | 6,458,135 | B1 | 10/2002 | Harwin et al. |
| 6,123,729 | A | 9/2000 | Insall et al. | 6,468,280 | B1 | 10/2002 | Saenger et al. |
| 6,126,692 | A | 10/2000 | Robie et al. | 6,478,799 | B1 | 11/2002 | Williamson |
| 6,126,693 | A | 10/2000 | O'Neil et al. | 6,479,565 | B1 | 11/2002 | Stanley |
| 6,139,581 | A | 10/2000 | Engh et al. | 6,488,687 | B1 | 12/2002 | Masini |
| 6,143,034 | A | 11/2000 | Burrows | 6,491,726 | B2 | 12/2002 | Pappas |
| 6,146,424 | A | 11/2000 | Gray, Jr. et al. | 6,494,914 | B2 | 12/2002 | Brown et al. |
| 6,152,935 | A | 11/2000 | Kammerer et al. | 6,500,179 | B1 | 12/2002 | Masini |
| 6,156,044 | A | 12/2000 | Kammerer et al. | 6,500,208 | B1 | 12/2002 | Metzger et al. |
| 6,159,216 | A | 12/2000 | Burkinshaw et al. | 6,503,254 | B2 | 1/2003 | Masini |
| 6,165,223 | A | 12/2000 | Metzger et al. | 6,506,193 | B1 | 1/2003 | Stubbs |
| 6,168,626 | B1 | 1/2001 | Hyon et al. | 6,506,215 | B1 | 1/2003 | Letot et al. |
| 6,168,629 | B1 | 1/2001 | Timoteo | 6,506,216 | B1 | 1/2003 | McCue et al. |
| 6,171,342 | B1 | 1/2001 | O'Neil et al. | 6,508,841 | B2 | 1/2003 | Martin et al. |
| 6,171,343 | B1 | 1/2001 | Dearnaley et al. | 6,514,259 | B2 | 2/2003 | Picard et al. |
| 6,174,314 | B1 | 1/2001 | Waddell | 6,520,964 | B2 | 2/2003 | Tallarida et al. |
| 6,176,607 | B1 | 1/2001 | Hajianpour | 6,520,996 | B1 | 2/2003 | Manasas et al. |
| 6,179,876 | B1 | 1/2001 | Stamper et al. | 6,527,807 | B1 | 3/2003 | O'Neil et al. |
| 6,184,265 | B1 | 2/2001 | Hamilton et al. | 6,528,052 | B1 | 3/2003 | Smith et al. |
| 6,187,010 | B1 | 2/2001 | Masini | 6,533,737 | B1 | 3/2003 | Brosseau et al. |
| 6,187,045 | B1 | 2/2001 | Fehring et al. | 6,539,607 | B1 | 4/2003 | Fehring et al. |
| 6,190,391 | B1 | 2/2001 | Stubbs | 6,554,838 | B2 | 4/2003 | McGovern et al. |
| 6,193,723 | B1 | 2/2001 | Cripe et al. | 6,558,391 | B2 | 5/2003 | Axelson, Jr. et al. |
| 6,197,064 | B1 | 3/2001 | Haines et al. | 6,558,393 | B1 | 5/2003 | Litwin et al. |
| 6,203,543 | B1 | 3/2001 | Glossop | 6,558,421 | B1 | 5/2003 | Fell et al. |
| 6,205,411 | B1 | 3/2001 | DiGioia, III et al. | 6,562,540 | B2 | 5/2003 | Saum et al. |
| 6,206,926 | B1 | 3/2001 | Pappas | 6,569,172 | B2 | 5/2003 | Asculai et al. |
| 6,206,927 | B1 | 3/2001 | Fell et al. | 6,569,202 | B2 | 5/2003 | Whiteside |
| 6,210,444 | B1 | 4/2001 | Webster et al. | 6,579,833 | B1 | 6/2003 | McNallan et al. |
| 6,210,445 | B1 | 4/2001 | Zawadzki | 6,589,248 | B1 | 7/2003 | Hughes |
| 6,214,011 | B1 | 4/2001 | Masini | 6,589,283 | B1 | 7/2003 | Metzger et al. |
| 6,217,615 | B1 | 4/2001 | Sioshansi et al. | 6,592,598 | B2 | 7/2003 | Vibe-Hansen et al. |
| 6,217,618 | B1 | 4/2001 | Hileman | 6,592,599 | B2 | 7/2003 | Vibe-Hansen et al. |
| 6,228,090 | B1 | 5/2001 | Waddell | 6,595,997 | B2 | 7/2003 | Axelson, Jr. et al. |
| 6,228,091 | B1 | 5/2001 | Lombardo et al. | 6,599,300 | B2 | 7/2003 | Vibe-Hansen et al. |
| 6,228,900 | B1 | 5/2001 | Shen et al. | 6,599,301 | B2 | 7/2003 | Vibe-Hansen et al. |
| 6,245,109 | B1 | 6/2001 | Mendes et al. | 6,599,321 | B2 | 7/2003 | Hyde, Jr. |
| 6,254,604 | B1 | 7/2001 | Howell | 6,602,258 | B1 | 8/2003 | Katz |
| 6,254,605 | B1 | 7/2001 | Howell | 6,602,259 | B1 | 8/2003 | Masini |
| 6,258,095 | B1 | 7/2001 | Lombardo et al. | 6,607,536 | B2 | 8/2003 | Litwin et al. |
| 6,258,096 | B1 | 7/2001 | Seki | 6,610,067 | B2 | 8/2003 | Tallarida et al. |
| 6,258,126 | B1 | 7/2001 | Colleran | 6,610,095 | B1 | 8/2003 | Pope et al. |
| 6,281,264 | B1 | 8/2001 | Salovey et al. | 6,616,696 | B1 | 9/2003 | Merchant |
| 6,283,980 | B1 | 9/2001 | Vibe-Hansen et al. | 6,620,168 | B1 | 9/2003 | Lombardo et al. |
| 6,290,704 | B1 | 9/2001 | Burkinshaw et al. | 6,620,198 | B2 | 9/2003 | Burstein et al. |
| 6,296,646 | B1 | 10/2001 | Williamson | 6,620,199 | B2 | 9/2003 | Grelsamer |
| 6,299,645 | B1 | 10/2001 | Ogden | 6,626,949 | B1 | 9/2003 | Townley |
| 6,302,916 | B1 | 10/2001 | Townley et al. | 6,627,141 | B2 | 9/2003 | McNulty et al. |
| 6,306,172 | B1 | 10/2001 | O'Neil et al. | 6,629,978 | B2 | 10/2003 | Schulzki et al. |
| 6,309,395 | B1 | 10/2001 | Smith et al. | 6,629,999 | B1 | 10/2003 | Serafin, Jr. |
| 6,319,283 | B1 | 11/2001 | Insall et al. | 6,637,437 | B1 | 10/2003 | Hungerford et al. |
| 6,342,061 | B1 | 1/2002 | Kauker et al. | 6,645,215 | B1 | 11/2003 | McGovern et al. |
| 6,342,075 | B1 | 1/2002 | MacArthur | 6,645,251 | B2 | 11/2003 | Salehi et al. |
| 6,355,045 | B1 | 3/2002 | Gundlapalli et al. | 6,652,587 | B2 | 11/2003 | Felt et al. |
| 6,355,067 | B1 | 3/2002 | Bloebaum | 6,652,592 | B1 | 11/2003 | Grooms et al. |

| | | |
|---|---|---|
| 6,660,039 B1 | 12/2003 | Evans et al. |
| 6,660,040 B2 | 12/2003 | Chan et al. |
| 6,673,077 B1 | 1/2004 | Katz |
| 6,677,415 B1 | 1/2004 | O'Connor et al. |
| 6,679,917 B2 | 1/2004 | Ek |
| 6,685,711 B2 | 2/2004 | Axelson, Jr. et al. |
| 6,685,743 B2 | 2/2004 | Komvopoulos et al. |
| 6,689,169 B2 | 2/2004 | Harris |
| 6,692,502 B1 | 2/2004 | Ertl et al. |
| 6,692,679 B1 | 2/2004 | McNulty et al. |
| 6,695,839 B2 | 2/2004 | Sharkey et al. |
| 6,702,821 B2 | 3/2004 | Bonutti |
| 6,709,460 B2 | 3/2004 | Merchant |
| 6,709,461 B2 | 3/2004 | O'Neil et al. |
| 6,709,464 B2 | 3/2004 | Scott et al. |
| 6,711,432 B1 | 3/2004 | Weiss et al. |
| 6,712,855 B2 | 3/2004 | Martin et al. |
| 6,712,856 B1 | 3/2004 | Carignan et al. |
| 6,716,248 B2 | 4/2004 | Huene |
| 6,719,800 B2 | 4/2004 | Meyers et al. |
| 6,726,727 B2 | 4/2004 | Scott et al. |
| 6,746,488 B1 | 6/2004 | Bales |
| 6,749,638 B1 | 6/2004 | Saladino |
| 6,755,864 B1 | 6/2004 | Brack et al. |
| 6,764,516 B2 | 7/2004 | Pappas |
| 6,770,077 B2 | 8/2004 | Van Zile et al. |
| 6,770,078 B2 | 8/2004 | Bonutti |
| 6,770,097 B2 | 8/2004 | Leclercq |
| 6,770,099 B2 | 8/2004 | Andriacchi et al. |
| 6,773,461 B2 | 8/2004 | Meyers et al. |
| 6,783,550 B2 | 8/2004 | MacArthur |
| 6,794,423 B1 | 9/2004 | Li |
| 6,797,005 B2 | 9/2004 | Pappas |
| 6,797,006 B2 | 9/2004 | Hodorek |
| 6,800,094 B2 | 10/2004 | Burkinshaw |
| 6,800,670 B2 | 10/2004 | Shen et al. |
| 6,802,867 B2 | 10/2004 | Manasas et al. |
| 2002/0138150 A1 | 9/2002 | Leclercq |
| 2003/0158606 A1 | 8/2003 | Coon et al. |
| 2003/0220697 A1 | 11/2003 | Justin et al. |

FOREIGN PATENT DOCUMENTS

| | | | |
|---|---|---|---|
| FR | 2 768 329 A | 3/1999 | |

MODULAR FEMORAL COMPONENT FOR A TOTAL KNEE JOINT REPLACEMENT FOR MINIMALLY INVASIVE IMPLANTATION

RELATIONSHIP TO OTHER APPLICATIONS

This application claims the benefit of U.S. Provisional Application Ser. No. 60/420,299, filed Oct. 23, 2002, the entire disclosure of which is incorporated herein by reference.

BACKGROUND OF THE INVENTION

1. Field of the Invention

This invention relates to joint replacement prostheses for the knee, and more particularly to such prostheses that can be implanted by minimally invasive surgical techniques.

2. Brief Description of the Prior Art

Replacement of diseased or damaged knees with suitable prostheses has become a common surgical procedure. The outcome of such surgery has been found to be favorable in most cases, and the surgery has come to be regarded as a very favorable surgical intervention for restoring function to knees damaged by trauma or degenerative disease. Each year more than 650,000 patients worldwide undergo operations in which either part or all of their knee joints is replaced, and the resulting implants typically operate well for 10 or more years. Typically, current designs consist of a metallic component made from a cobalt-based alloy to replace the bearing surfaces of the femur. This femoral prosthesis bears upon an ultra-high molecular weight polyethylene component implanted upon the proximal end of the tibia. Additionally a second polyethylene implant is used to replace the undersurface of the patella so that it slides upon the central region of the metallic femoral implant. To minimize the problem of wear in the joints, the metallic component is polished to a very fine mirrored surface and the bearing surfaces are designed with a high degree of conformity to reduce contact stresses.

One of the major problems with the conventional procedure, however, is that the prostheses are relatively large, and, accordingly, must be inserted through relatively long incisions. Specifically, the large metal component that comprises the femoral implant is generally about four inches wide and about three inches high, which requires a correspondingly large incision for implantation. Such large incisions tend to disrupt the tissues associated with the joint and its joint capsule, requiring long healing and rehabilitation periods after the operation before the patient can return to normal activities. Although surgeons have recognized the desirability of minimizing the size of the incisions, the large size of the prostheses of current design have frustrated attempts to use smaller incisions, e.g., 1-2 inches in length.

U.S. Published Patent Application No. 2003/0158606, to Coon et al., discloses a knee arthroplasty prosthesis wherein a femoral component of a total knee joint replacement is made in more than one piece. The pieces are inserted separately and assembled within the surgical site. The separate pieces of the femoral component are provided with mating surfaces generally formed at an angle to a plane oriented in an anterior-posterior direction and proximal distal direction with respect to the femur. However, the multi-piece prosthesis of Coon is disclosed as requiring a surgical incision of three inches.

Accordingly, a need has continued to exist for a knee joint prosthesis that can be inserted using minimally invasive surgical techniques.

SUMMARY OF THE INVENTION

The problem of excessive trauma to the knee joint during implantation of a knee prosthesis has now been alleviated by the modular femoral component for a total knee joint replacement of this invention, which is capable of being inserted and implanted through surgical procedures that are significantly less invasive than the conventional procedures.

According to the invention the femoral component of the total knee joint replacement is provided in multiple segments or modules that can be separately inserted through minimally invasive incisions and subsequently assembled within the joint to form a functioning unit.

Accordingly it is an object of the invention to provide a modular femoral component for a total knee joint replacement.

A further object is to provide a femoral component for a total knee joint replacement that can be inserted using minimally invasive surgical techniques.

A further object is to provide a femoral component for a total knee joint replacement that can be inserted through a relatively small incision.

A further object is to provide a femoral component for a total knee joint replacement that can be inserted through a relatively small incision and assembled within the joint to form a functioning prosthesis.

A further object is to provide a femoral component for a total knee joint replacement that is less traumatic to the knee joint than currently used prostheses.

A further object is to provide a femoral component for a total knee joint replacement that permits faster rehabilitation after surgery.

Further objects of the invention will become apparent from the description which follows.

DETAILED DESCRIPTION OF THE INVENTION AND PREFERRED EMBODIMENTS

The present invention comprises a design of a total knee prosthesis in which the femoral component is provided in multiple pieces or modules sized for insertion through a minimally invasive incision and capable of assembly within the joint to form a single functioning unit. The individual modules are provided with alignment structure, e.g., mating projections and recesses. The modules are held together by fastening structures, e.g., screws, interfitting joints, interference joints, and the like.

Accordingly, the femoral prosthesis of the invention for use as a component of an artificial knee joint comprises a plurality of segments or modules, each of said segments having a femoral fixation surface adapted to be positioned on a distal end of a femur and at least one assembly surface adapted to be joined to an assembly surface of an adjacent one of said segments or modules.

The modular prosthesis of the invention may comprise any convenient number of modules that, when assembled within the surgically prepared region of the joint, will form a functional prosthesis on the distal end of the femur. At least some of the individual modules of the modular prosthesis have a femoral fixation surface that is adapted to contact the surgically prepared distal end of the femur and be attached by conventional methods such as an appropriate cement, mechanical fastener or the like.

Figure 2A:
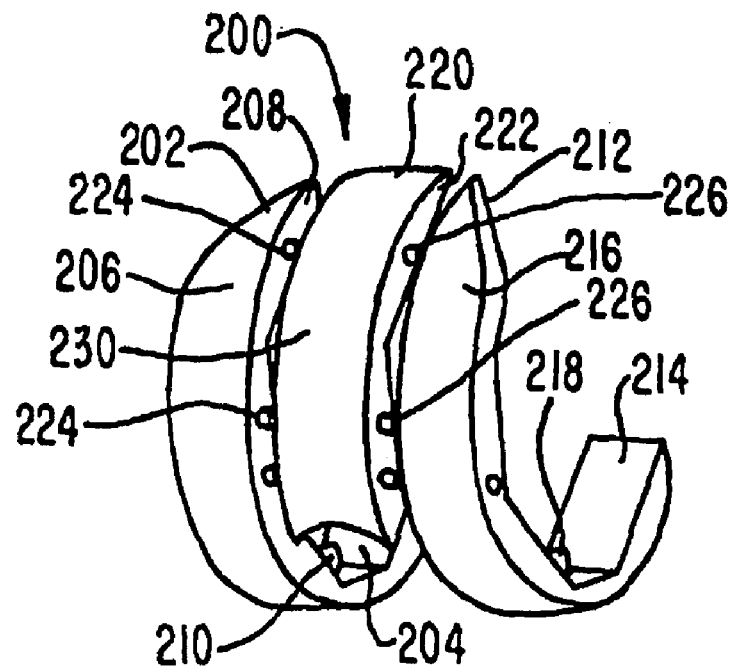
FIG. 2A illustrates a modular femoral component for a total knee joint replacement of another embodiment of the invention in a disassembled state.
Figure 2B:
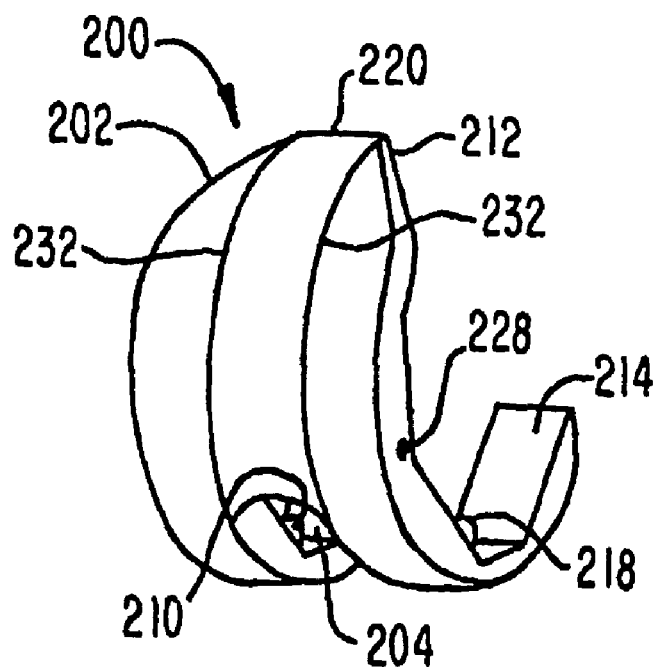
FIG. 2B illustrates a modular femoral component for a total knee joint replacement of the embodiment of FIG. 2A in an assembled state.

Although the modular prosthesis of the invention may comprise any convenient number of modules, preferred embodiments may include two or three modules as illustrated in the drawings. Not all modules have to have a femoral fixation surface; some of the modules may serve as spacers between other modules, as is illustrated in FIGS. 2A and 2B, discussed in more detail below.

The side of the module generally opposite to the femoral fixation surface is a bearing surface that contacts a corresponding prosthesis affixed to the proximal end of the tibia in order to bear the weight imposed on the joint and transfer the force to the tibia. The bearing surface of each module is shaped and configured to provide a generally conventional femoral prosthetic surface when the modular prosthesis is assembled. The bearing surface is also provided with the conventional highly polished surface in order to minimize friction within the joint.

Each module is also provided with at least one assembly or mating surface that contacts and mates with a corresponding assembly or mating surface of an adjacent module. The assembly surfaces of adjacent modules are shaped and configured so that a secure and rigid fastening therebetween is possible. Any conventional structure for holding such mating surfaces together may be used. For example, the mating surfaces can be generally planar and the modules can be provided with holes or passageways through which alignment pins or screws can be passed to align and/or fasten the modules securely together. Adjacent mating faces may be provided with projecting alignment pins, lugs, or the like, adapted to mate with corresponding recesses on the mating face of an adjacent module. Alternatively, the mating faces can be provided with joining features that both align and secure the modules, such as dovetail joints, interference fit joints, and the like. Instead of discrete lugs, the entire mating surfaces of adjacent modules can be designed as male and female lugs. Such an arrangement with large contacting alignment surfaces may be expected to increase the shear strength of the joint and thereby contribute to the rigidity of the prosthesis. The mating surfaces need not be planar. The mating surfaces are generally of complementary shape over a sufficient portion of their surface areas in order to provide for a secure and rigid assembly of the modules. It is preferred to design the assembly surfaces so that they are self-aligning as they are assembled within the surgically prepared knee joint. Such self-aligning mating surfaces can be achieved, for example, by providing tapered alignment lugs, pins, or the like, on one of the mating surfaces that fit into similarly tapered recesses in the complementary mating surface. Alternatively the mating surfaces can deviate somewhat from strict planarity, with complementary surface profiles so that they will assume a single orientation as they are pressed together. For example, one of the assembly surfaces may have a relatively shallow broad based V-shape configuration, extending over the entire surface or a portion of the area thereof, while the mating surface may have a complementary V-shaped depressed configuration, so that the surfaces would gradually slip into their final alignment as they are brought together within the surgical site. Such self-aligning configuration of the assembly surfaces enhances the ease of assembly within a surgical site that is confined and not subject to easy direct observation. Other such mechanisms for achieving self-aligning mating surfaces are readily visualized by those skilled in the art.

The dimensions of the segments of the femoral component of the invention are set so that the assembled femoral component has a size within the conventional size range of integral currently used femoral components of total knee joint replacement prostheses. To this end the individual segments have dimensions proportioned to the dimensions of standard femoral components (which are provided in various sizes to accommodate different-sized individual patients). Thus for a two-segment femoral component of the invention the individual segments may range in width between about one-third and about two thirds of the lateral dimensions of a standard one-piece femoral component. The basis for the variation may involve relative ease of insertion. For example it may be easier to insert a smaller segment deep into the surgical site and follow with a somewhat larger segment. The basis for the variation may also involve the location chosen by the surgeon to place the articulation between the segments, e.g., exactly in the center of the patellar groove, or somewhat to one side of the center, as may be required or desirable in an individual patient. Accordingly in a three-segment femoral component according to the invention the segments may range in width from about somewhat less than one-third of the width of a conventional unitary femoral component to about as much as two-thirds of the width of a conventional femoral component. For example, the width of the central segment may be chosen to be somewhat greater than one-third of the width of a conventional one-piece femoral component or somewhat less than about one-third of the width of a conventional femoral component.

If separate fasteners are used for securing the modules together they may be of any conventional type, such as screws, rivets, or the like.

The mating surfaces can be formed at any convenient angle to the femoral fixation surfaces and/or the bearing surfaces. However, for convenient assembly during the surgical procedure it is preferred that the mating surfaces are oriented generally perpendicularly to the femoral fixation surfaces and bearing surfaces and extend generally in the proximal-distal direction relative to the femur. Such a preferred orientation is illustrated in the accompanying drawings.

In general, the articulation between two segments of the femoral component of the invention, i.e., the line at a surface, e.g., a bearing surface, of the femoral component where the mating surfaces meet should be positioned and aligned to minimize contact with the overlying patella or patellar component of the knee joint replacement. In preferred embodiments the articulation is located away from the peak of the condylar portion of the femoral component and preferably in the groove between the condylar portions. It is also preferred that the articulation be arranged in a longitudinal direction with respect to the femur, i.e., in a proximal-distal direction, to minimize motion of the patella or patellar component transverse to the line of articulation as the total knee replacement is flexed and extended. This requirement is highly preferred for those areas of the femoral component wherein the pressure of the overlying patella or patellar component is relatively great. The condition can be somewhat relaxed in those areas of the femoral component where the patellar pressure is somewhat less. In such areas, the articulation may be oriented to permit some cross-motion, especially if other benefits, e.g., greater strength or rigidity or greater ease of assembly can be achieved.

Figure 4A:
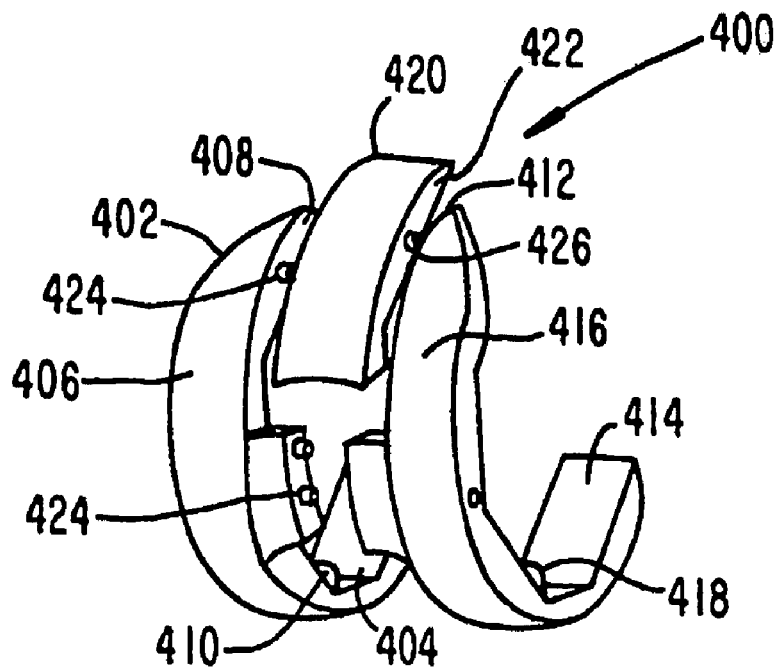
FIG. 4A illustrates a modular femoral component for a total knee joint replacement of another embodiment of the invention wherein the central segment is present only in the upper portion of the femoral component, while the outer segments are joined together in the lower portion of the femoral component.
Figure 4B:
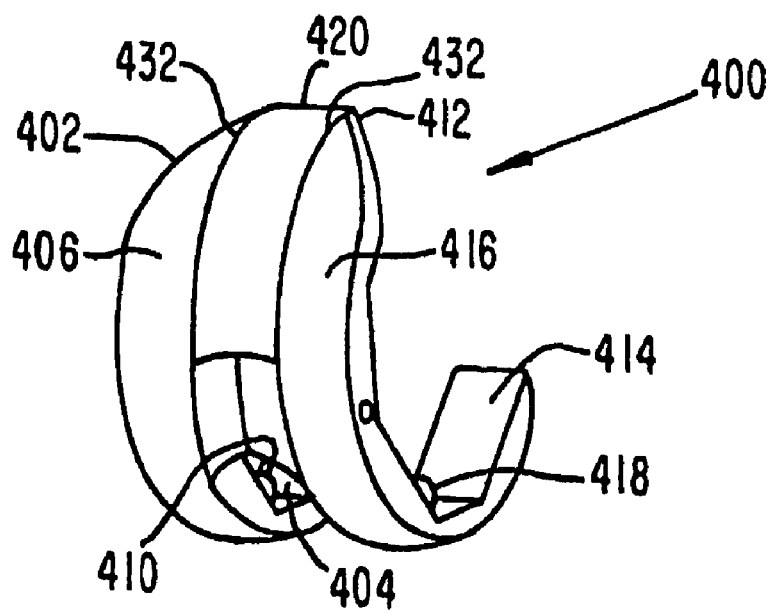
FIG. 4B illustrates a modular femoral component for a total knee joint replacement of the embodiment of FIG. 4A in an assembled state.

In an alternate embodiment wherein the femoral component of the invention is assembled from three segments, a central segment may be present which extends only partway along the height of the femoral component. The two outer segments may then be joined to one another via mating surfaces extending the remainder of the height of the femoral component. Such an embodiment is illustrated in FIGS. 4A and 4B, discussed in more detail below.

The modular prosthesis of the invention may be made of any conventional material used in such prostheses. Thus, the individual modules may be made of metal such as titanium, or a cobalt-based alloy or the like, or of a ceramic such as alumina, zirconia, or the like.

The modules of the prosthesis may be manufactured by any appropriate conventional techniques for processing metal or ceramic objects such as machining, casting, forging, hot isostatic pressing, sintering, grinding, or the like.

The modular prosthesis of the invention will be illustrated by the accompanying drawings which illustrate certain embodiments and features of the invention, but are not intended to limit the scope of the invention which is defined solely by the appended claims.

Figure 1A:
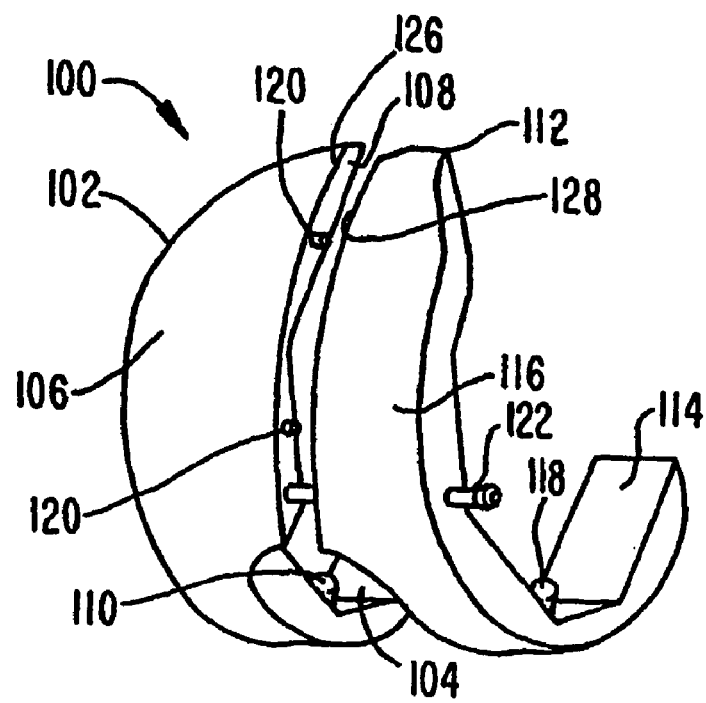
FIG. 1A illustrates a modular femoral component for a total knee joint replacement of one embodiment of the invention in a disassembled state.

FIG. 1A illustrates one embodiment 100 of the modular prosthesis of the invention in a disassembled configuration. The modular prosthesis 100 comprises a first module 102, having a femoral fixation surface 104, a bearing surface 106 for contacting an opposed mating surface on a tibial prosthesis (not shown), and a mating face 108 for mating with a corresponding mating face of the second module 112. The femoral fixation surface 104 is provided with one or more locating and fixing projections 110 which fit into corresponding recesses surgically formed in the distal end of the femur. The second module 112 of the modular prosthesis 100 comprises a femoral fixation surface 114, a bearing surface 116 for contacting an opposed mating surface on a tibial prosthesis (not shown). The second module also has a mating face (not visible) for mating with the corresponding mating face 108 of the first module 102. The first module 102 of the modular prosthesis 100 is also provided with one or more alignment pins 120 for engaging corresponding alignment recesses or holes (not shown) in the mating face of the second module 112, and with one or more fastener screws 122 for holding the assembled modules 102, 112 of the prosthesis 100 securely together.

Figure 1B:
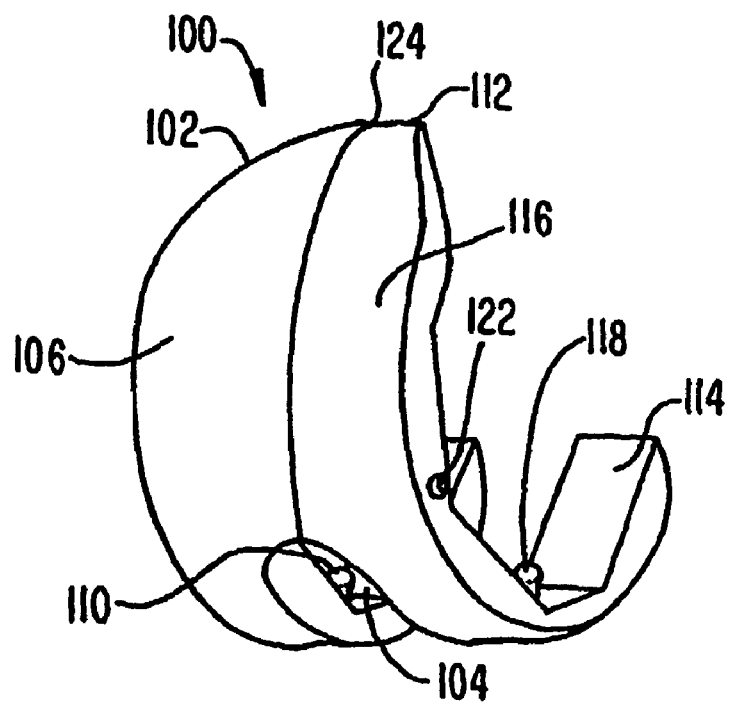
FIG. 1B illustrates a modular femoral component for a total knee joint replacement of the embodiment of FIG. 1A in an assembled state.

FIG. 1B shows the modular prosthesis 100 of FIG. 1A in its assembled configuration, wherein mating surface 108 of the first module 102 and the corresponding mating surface (not shown) of the second module 112 are held securely together by fastener screw 102 as indicated by mating line 124.

FIG. 2A illustrates another embodiment 200 of the modular prosthesis of the invention in a disassembled configuration. The modular prosthesis 200 comprises a first module 202, having a femoral fixation surface 204, a bearing surface 206 for contacting an opposed mating surface on a tibial prosthesis (not shown), and a mating face 208 for mating with a corresponding mating face of the third module 220. The femoral fixation surface 204 is provided with one or more locating and fixing projections 210 which fit into corresponding recesses surgically formed in the distal end of the femur. The second module 212 of the modular prosthesis 200 comprises a femoral fixation surface 214, a bearing surface 216 for contacting an opposed mating surface on a tibial prosthesis (not shown). The second module also has a mating face (not visible) for mating with the corresponding mating face 222 of the third module 220. The first module 202 of the modular prosthesis 200 is also provided with one or more alignment pins 220 for engaging corresponding alignment recesses or holes (not shown) in the mating face of the third module 220, and the third module 220 is provided with one or more alignment pins 226 for engaging corresponding alignment recesses or holes in the mating face (not shown) of the second module 212. One or more fastener screws 228 hold the assembled modules 202, 212, and 220 of the prosthesis 100 securely together.

FIG. 2B shows the modular prosthesis 200 of FIG. 2A in its assembled configuration, wherein mating surfaces 208 of the first module 202 and 222 of the third module 220 are held securely together with the corresponding mating surfaces (not shown) of the third module 220 and the second module 212, respectively, by fastener screw 228 as indicated by mating lines 232.

Figure 3A:
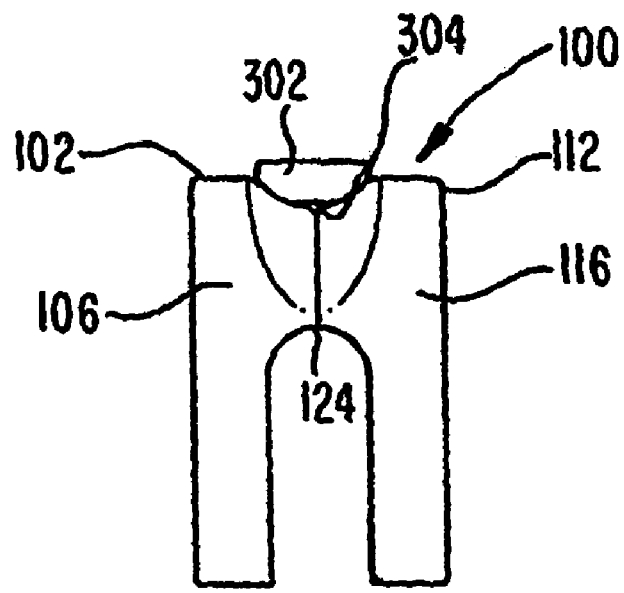
FIG. 3A is a front elevational view of the femoral component of FIG. 1B showing the articulation of the prosthesis with the undersurface of the patella or an undersurface patellar implant.
Figure 3B:
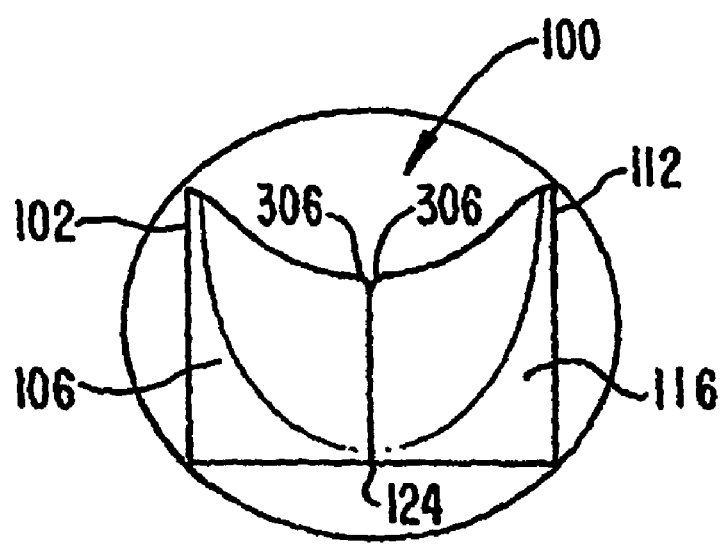
FIG. 3B is an enlarged view of the assembled femoral component of FIG. 1B showing the recessed or beveled interface between adjacent modules.

FIG. 3A shows a front elevational view of the modular prosthesis 100 of FIGS. 1A and 1B, illustrating the interaction of the bearing surfaces 106 and 116 with the mating or contacting surface 304 of the patella 302. In order to prevent contact of any tissue or plastic covering associated with the surface 304 of the patella 302 with a sharp or rough exposed edge of a mating surface 108 of the first module 102 or the corresponding mating surface of second module 112, the edges 126, 128 of the mating surfaces are provided with beveled or radiused corners 306 so that the mating line 124 is depressed below the bearing surfaces 102 and 112. This construction assures that adjacent tissue may move over the mating line 124 of the modules 102 and 112 without being torn, abraded, or otherwise injured and that any plastic covering, e.g., of polyethylene or the like, associated with the lower surface of the patella will not be roughened or abraded.

FIG. 4A illustrates another embodiment 400 of the modular prosthesis of the invention in a disassembled configuration. In this embodiment 400 the central segment contacts the side segments with assembly surfaces that extend partway down the height of the femoral component of the invention. The modular prosthesis 400 comprises a first module 402, having a femoral fixation surface 404, a bearing surface 406 for contacting an opposed mating surface on a tibial prosthesis. (not shown), and a mating or assembly face 408 for mating with a corresponding mating face of the third module 420. The femoral fixation surface 404 is provided with one or more locating and fixing projections 410 which fit into corresponding recesses surgically formed in the distal end of the femur. The second module 412 of the modular prosthesis 400 comprises a femoral fixation surface 414, a bearing surface 416 for contacting an opposed mating surface on a tibial prosthesis (not shown). The femoral fixation surface 404 is provided with one or more locating and fixing projections 418 which fit into corresponding recesses surgically formed in the distal end of the femur. The second module also has a mating face (not visible) for mating with the corresponding mating face 422 of the third module 420. The first module 402 of the modular prosthesis 400 is also provided with one or more alignment pins, 424 for engaging corresponding alignment recesses or holes (not shown) in the mating face of the third module 420, and the third module 420 is provided with one or more alignment pins 426 for engaging corresponding alignment recesses or holes in the mating face (not shown) of the second module 412. One or more fastener screws 428 hold the assembled modules 402, 412, and 420 of the prosthesis 400 securely together.

FIG. 2B shows the modular prosthesis 400 of FIG. 2A in its assembled configuration, wherein mating surfaces 408 of the first module 402 and 422 of the third module 420 are held securely together with the corresponding mating surfaces (not shown) of the third module 420 and the second module 412, respectively, by fastener screw 228 as indicated by mating lines 432.

The invention having been disclosed above in connection with certain embodiments it is to be understood that all changes and modifications that, conform to the disclosure and spirit of the invention are to be considered as included therein, the scope of the invention being defined by the appended claims.

We claim:

1. A femoral component for a total knee joint replacement comprising,
    a plurality of segments, each of said segments having a femoral fixation surface adapted to be positioned on a distal end of a femur and at least one assembly surface adapted to be joined to an assembly surface of an adjacent one of said segments said assembly surface being generally planar and arranged to be oriented generally in a plane extending in a proximal-distal direction and in an anterior-posterior direction when said femoral fixation surface is positioned on said distal end of said femur,
    wherein at least two adjacent segments each comprise a bearing surface on an anterior portion of said component, said assembly surfaces of said segments being in mutual contact and said bearing surfaces of said adjacent segments being positioned to form a generally continuous bearing surface on an anterior portion of said component,
    wherein edges of said mutually contacting assembly surfaces on portions of the assembly surfaces closest to the generally continuous bearing surface are recessed below said generally continuous bearing surface on an anterior portion of said component,
    wherein each of said plurality of segments is configured to be separately inserted through an incision in a person and assembled to another of the plurality of segments after insertion through the incision,
    wherein the assembly surface of each segment has a beveled corner.

2. The femoral component for a total knee joint replacement of claim 1, additionally comprising:
    at least one fastener holding said assembly surfaces in mutual contact.

3. The femoral component for a total knee joint replacement of claim 2, further comprising at least one bolt that connects the segments, wherein the assembly surfaces of the segments have holes through which the bolt can be passed to align and fasten the segments together.

4. The femoral component for a total knee joint replacement of claim 1, wherein said assembly surfaces are provided with self-alignment structures.

5. The femoral component of a total knee joint replacement of claim 4, wherein said self-alignment structures are at least one projection on a first one of said assembly surfaces and at least one complementary depression on a second one of said assembly surfaces adapted to mate with said first one of said assembly surfaces.

6. The femoral component for a total knee joint replacement of claim 5, wherein the at least one projection includes a pin.

7. The femoral component for a total knee joint replacement of claim 6, wherein the pin is tapered.

8. The femoral component for a total knee joint replacement of claim 5, wherein the at least one projection has a v-shape configuration and the at least one complementary depression has a v-shape depressed configuration.

9. The femoral component for a total knee joint replacement of claim 4, wherein the self-alignment structures secure the segments together.

10. The femoral component for a total knee joint replacement of claim 9, wherein the self-alignment structures include one of a dovetail joint and an interference fit joint.

11. The femoral component for a total knee joint replacement of claim 1, wherein the segments are each formed of one of titanium, cobalt-based alloy, alumina, and zirconia.

12. The femoral component for a total knee joint replacement of claim 1, wherein the assembly surface of each segment is oriented generally perpendicularly to the femoral fixation surface and the bearing surface of the segment.

13. The femoral component for a total knee joint replacement of claim 1, wherein the assembly surfaces of the segments are positioned to minimize contact with one of an overlying patella and an overlying patellar component.

14. The femoral component for a total knee joint replacement of claim 1, including a condylar portion with a peak, wherein the assembly surfaces are positioned away from the peak.

15. The femoral component for a total knee joint replacement of claim 1, including two condylar portions with a groove between the condylar portions, wherein the assembly surfaces are positioned in the groove.

16. The femoral component for a total knee joint replacement of claim 1, wherein the edges of said mutually contacting assembly surfaces form a mating line that is recessed below said generally continuous bearing surface on the anterior portion of said component.

* * * * *